United States Patent [19]

Nadelson

[11] 4,024,262
[45] May 17, 1977

[54] SUBSTITUTED HYDROXY PYRIDONES

[75] Inventor: Jeffrey Nadelson, Lake Parsippany, N.J.

[73] Assignee: Sandoz, Inc., E. Hanover, N.J.

[22] Filed: Mar. 5, 1976

[21] Appl. No.: 664,237

Related U.S. Application Data

[63] Continuation-in-part of Ser. No. 602,324, Aug. 6, 1975, abandoned.

[52] U.S. Cl. .......................... 424/263; 260/296 H; 260/297 Z; 260/307 H
[51] Int. Cl.² ........................................ A61K 31/44
[58] Field of Search ....... 260/296 R, 297 Z, 296 H, 260/307 H; 424/263

[56] References Cited

UNITED STATES PATENTS

| | | | |
|---|---|---|---|
| 2,431,190 | 11/1947 | Morgan | 260/296 R X |
| 3,541,101 | 11/1970 | Markillie | 260/288 |
| 3,736,327 | 5/1973 | Denzel et al. | 260/296 H |
| 3,816,421 | 6/1974 | Gibbons et al. | 260/256.4 F |

*Primary Examiner*—John D. Randolph
*Attorney, Agent, or Firm*—Gerald D. Sharkin; Robert S. Honor; Timothy G. Rothwell

[57] ABSTRACT

Substituted hydroxy pyridones, e.g., 3-(1-iminopropyl)-4-hydroxy-6-phenyl-1-methyl-2-(1H)-pyridone, are prepared by reducing corresponding isoxazolo[4,5-c]pyridin-4(5H)-ones and are useful as minor tranquilizers, sleep inducers and neuroleptics.

9 Claims, No Drawings

SUBSTITUTED HYDROXY PYRIDONES

This application is a continuation-in-part of copending application Ser. No. 602,324, filed Aug. 6, 1975 now abandoned.

This invention relates to substituted hydroxy pyridones which exhibit minor tranquilizer, sleep inducer and neuroleptic activity. In particular, it relates to 3-iminoalkyl-4-hydroxy-6-substituted or unsubstituted phenyl-1-substituted-2-(1H)-pyridones, intermediates thereof and pharmaceutically acceptable salts thereof.

The compounds of this invention may be represented by the following structural formula

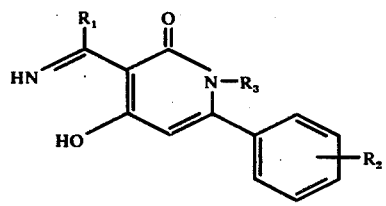
(I)

wherein
R₁ represents lower alkyl, i.e., alkyl having 1 to 4 carbon atoms, e.g., methyl, ethyl, isopropyl and the like, or cycloalkyl, i.e., cycloalkyl having 3 to 6 carbon atoms, e.g., cyclopropyl, cyclobutyl and the like, R₂ represents hydrogen, halo having an atomic weight of about 19 to 36, lower alkyl as defined above, or lower alkoxy, i.e., alkoxy having 1 to 4 carbon atoms, e.g., methoxy, ethoxy and the like, and R₃ represents straight chain lower alkyl, i.e., straight chain alkyl having 1 to 4 carbon atoms, e.g., methyl, ethyl, propyl and the like.

The compounds of formula (I) are prepared according to the following reaction scheme:

where R₁, R₂ and R₃ are as defined above.

The compounds of formula (I) are prepared by reducing a compound of the formula (II) under hydrogen gas in the presence of a catalyst and an inert organic solvent. Although the particular hydrogenation catalyst employed is not critical, the preferred catalysts include palladium on carbon, platinum oxide, Raney nickel, and the like, preferably palladium on carbon. The particular solvent used is not critical, but it is preferred that the reaction be run in the presence of the lower alkanols, e.g., methanol, ethanol, and the like, preferably ethanol. The temperature of the reaction is not critical, but it is preferred that the reaction be run from about 10° to 50° C., preferably from about 20° to 30° C. The reaction is run from about 1 to 10 hours, preferably from about 2 to 3 hours. The product is recovered using conventional techniques, e.g., filtration.

The compounds of formula (II) are prepared according to the following reaction scheme:

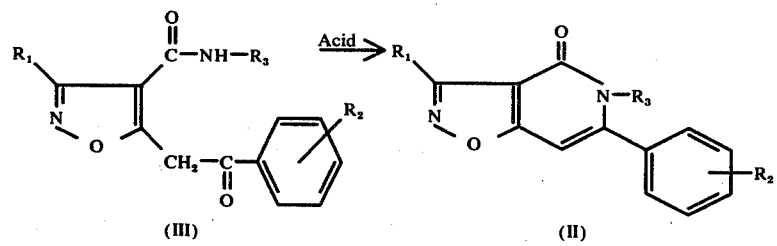
(III) (II)

where R₁, R₂ and R₃ are as defined above.

The compounds of formula (II) are prepared by treating a compound of the formula (III) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being especially preferred. The temperature of the reaction is not critical, but it is preferred that the reaction be run from about 80° to 150° C., preferably the reflux temperature of the solvent. The reaction is run from about 12 to 36 hours, preferably from about 20 to 36 hours. The product is recovered using conventional techniques, e.g., trituration followed by recrystallization.

The compounds of formula (III) are prepared according to the following reaction scheme:

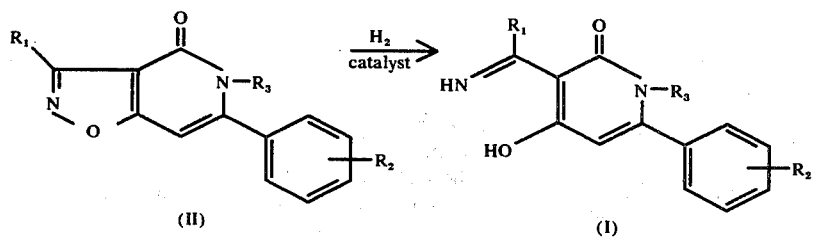
(II) (I)

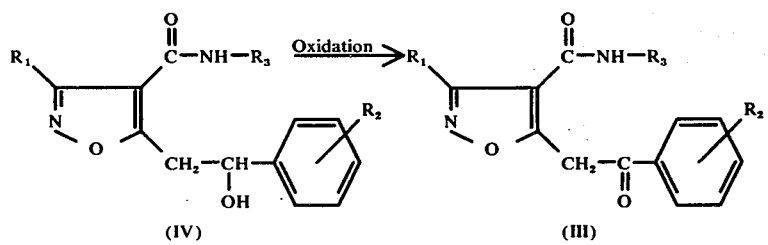

where $R_1$, $R_2$ and $R_3$ are as defined above.

The compounds of formula (III) are prepared by treating a compound of the formula (IV) with an oxidizing agent such as chromium trioxide, potassium permanganate, and the like, preferably chromium trioxide, under acidic conditions in the presence of water. Although the particular acid employed is not critical, the preferred acids include the mineral acids such a sulfuric acid, hydrochloric acid or acetic acid, the latter being especially preferred. The particular solvent employed is critical, and water is the only solvent contemplated in this reaction. The temperature of the reaction is not critical, but it is preferred that the reaction be run from about 10° to 50° C., preferably from about 20° to 30° C. The reaction is run from about 1 to 5 hours, preferably from about 1.5 to 2.5 hours. The product is recovered using conventional techniques, e.g., trituration followed by filtration.

The compounds of formula (IV) are prepared according to the following reaction scheme:

recovered using conventional techniques, e.g., trituration followed by filtration.

The compounds of formula (V) are prepared according to the following reaction scheme:

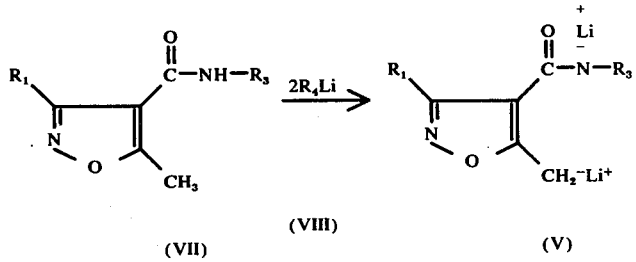

where $R_4$ is lower alkyl having 1 to 4 carbon atoms, and $R_1$ and $R_3$ are as defined above.

The compounds of formula (V) are prepared by treating a compound of the formula (VII) with a compound of the formula (VIII) in the presence of an inert organic solvent. Although the particular solvent employed is not critical, the preferred solvents include an ether such as diethylether or tetrahydrofuran as an aliphatic hydrocarbon such as pentane, hexane, heptane and the like, preferably hexane. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product of the compound of formula (VII) is not isolated but employed in situ as

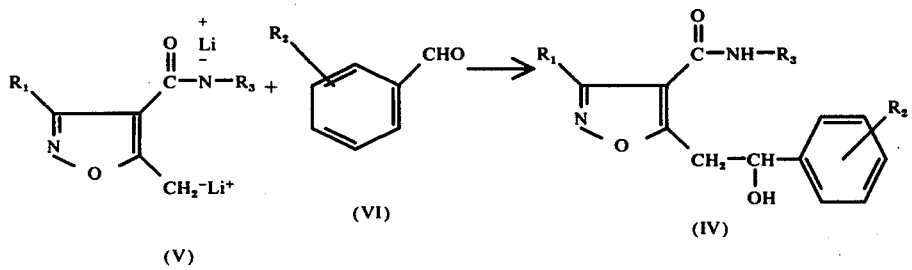

where $R_1$, $R_2$ and $R_3$ are as defined above.

The compounds of formula (IV) are prepared by treating a compound of the formula (V) with a compound of the formula (VI) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably tetrahydrofuran. The temperature of the reaction is not critical, but it is preferred that the reaction be run at a temperature of from about −75° to −55° C., preferably from about −65° to −60° C. The reaction is run from about 1 to 5 hours, preferably from about 2.5 to 3.5 hours. The product is a starting material in the preparation of the compounds of formula (IV).

The compound of formula (I) may also exist in the following tautomeric forms, and these tautomeric forms are also included within the scope of this invention:

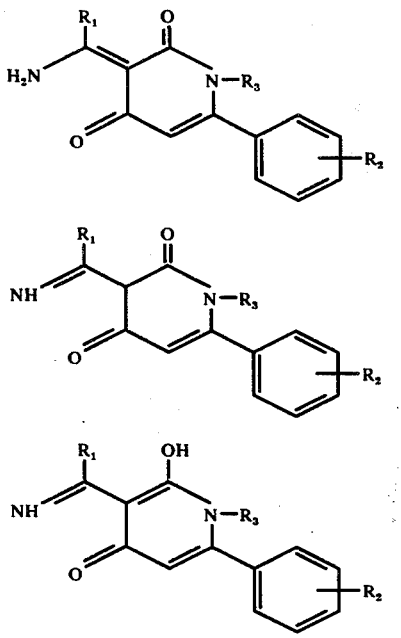

where $R_1$, $R_2$ and $R_3$ are as defined above.

Many of the compounds of formulae (VI), (VII) and (VIII) are known and may be prepared by methods described in the literature. The compounds of formulae (VI), (VII), and (VIII) not specifically described may be prepared by analogous methods from known starting materials.

The compounds of formula (I) are useful because they possess pharmacological activity in animals as sleep inducers, minor tranquilizers and neuroleptics as indicated (1) by the hexobarbital reinduction method of Winter, J. Pharmacol. and Exp. Therap., 94, 7–11, 1948, in which the reinduction of anethesia is used to determine sedative-hypnotic activity in mice given 70 mg/kg of animal body weight i.p. of hexobarbital followed immediately after the mice regain their righting reflexes by 4 to 200 mg/kg of animal body weight i.p. of the test compound; (2) by their ability to produce docility in behavior tests in mice given 20 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (3) by their ability to antagonize chronic convulsions and death in mice given about 35 to 250 mg/kg of the test compound followed immediately by 50 mg/kg i.p. of N-sulfamoylazepine; (4) by the apomorphine gnawing test basically as described by the method of Ernst (Psychopharmacologica, 10:316 to 323, 1967) in which male wistar rats weighing 90 to 110 g. are given 17.3 mg/kg p.o. of the test compound followed 30 minutes later by 10 mg/kg. i.p. of apomorphine. It is well known that gnawing is induced by apomorphine and the test compound is said to have neuroleptic activity if it reduces the gnawing activity in rats; and (5) by the rat conditioned avoidance response methodology of L. Cook and C. Cantania, Effects of Drugs on Avoidance and Escape Behavior, Federation Proceedings, Vol. 23, 818–825, (1964) in which rats are administered orally 22.0 mg/kg of the test compound. After administration, if the compound blocks the avoidance response, said compound is said to be a neuroleptic agent.

The sleep-inducing effective dosage of the compounds of formula (I) will vary depending on the particular compound employed. However, in general, satisfactory results are obtained when the compounds are administered orally at a daily dosage of from about 1.0 milligrams to about 100 milligrams per kilogram of animal body weight, typically given in a single dose at bedtime. For most large mammals, the total daily dosage is from about 15 to about 750 milligrams, preferably at bedtime, and dosage forms suitable for internal administration comprise from about 3.5 to about 375 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use, the effective dosage will vary depending on the particular compound employed. However, in general, satisfactory results are obtained when the compounds are administered orally at a daily dosage of from about 1.0 milligrams to about 100 milligrams per kilogram of animal body weight, typically given in divided doses two to four times per day. For most large mammals, the total daily dosage is from about 10 to about 1000 milligrams, and dosage forms suitable for internal administration comprise from about 2.5 to about 500 milligrams of the compound in admixture with a solid or liquid pharmaceutical carrier or diluent.

For neuroleptic use, the effective dosage will vary depending on the particular compound employed. However, in general, satisfactory results are obtained when the compounds are administered orally at a daily dosage of from about 1.0 milligrams to about 100 milligrams per kilogram of animal body weight, typically given in divided doses two to four times per day. For most large mammals, the total daily dosage is from about 1 to about 1000 milligrams and dosage forms suitable for internal administration comprise from about 0.25 to about 500 milligrams of the compound in admixture with a solid or liquid pharmaceutical carrier or diluent.

The compounds of formula (I) may be similarly administered in the form of their non-toxic pharmaceutically acceptable salts. Such salts possess the same order of activity as the non-salt form and are readily prepared by reacting the molecule with an appropriate acid or an appropriate base by conventional technique and, accordingly, are included within the scope of this invention. Representative of such salts are the mineral acid salts, e.g., hydrochloride, hydrobromide, sulfate and the like, and the alkali metal salts such as sodium, potassium and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers and neuroleptics in divided doses two to four times per day.

| Ingredients | Weight (mg.) | |
|---|---|---|
| | Tablet | Capsule |
| 3-(1-iminopropyl)-4-hydroxy-6-phenyl- | | |

-continued

| Ingredients | Weight (mg.) | |
|---|---|---|
| | Tablet | Capsule |
| 1-methyl-2(1H)-pyridone | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

3-Ethyl-5-(β-hydroxyphenethyl)-N-methyl-isoxazole-4-carboxamide.

A suspension of 58.5 g. (0.348 mole) of 3-ethyl-N,5-dimethyl-isoxazole-4-carboxamide and 1 liter of tetrahydrofuran is cooled to −65° C. and 478 ml. of 1.6M n-butyllithium in hexane (0.765 mole) is added dropwise maintaining the temperature between −60° and −70° C. After the addition is complete, the suspension is stirred for 1½ hours at −60° to −70° C., and then 37.2 g. (0.350 mole) of benzaldehyde in 375 ml. tetrahydrofuran is added dropwise maintaining the temperature between −60° and −70° C. After addition is complete, the mixture is stirred for 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous mangesium, sulfate, filtered and evaporated in vacuo. The solid residue is triturated with ether and filtered to give 3-ethyl-5-(β-hydroxyphenethyl)N-methyl-isoxazole-4-carboxamide, m.p. 135° to 137° C.

Following the above procedure and using in place of 3-ethyl-N,5-dimethyl-isoxazole-4-carboxamide, an equivalent amount of
  (a) 3-cyclohexyl-N,5-dimethyl-isoxazole-4-carboxamide,
there is obtained
  (a) 3-cyclohexyl-5-(β-hydroxyphenethyl)-N-methyl-isoxazole-4-carboxamide.

Again following the same procedure and using in place of benzaldehyde an equivalent amount of
  (b) p-chlorobenzaldehyde,
  (c) p-fluorobenzaldehyde,
  (d) p-methylbenzaldehyde,
  (e) p-methoxybenzaldehyde,
  (f) m-fluorobenzaldehyde,
  (g) o-fluorobenzaldehyde, or
  (h) o-methylbenzaldehyde
there is obtained
  (b) 3-ethyl-5-(4-chloro-β-hydroxyphenethyl)-N-methyl
  (c) isoxazole-4-carboxamide,
  (c) 3-ethyl-5-(4-fluoro-β-hydroxyphenethyl)-N-methylisoxazole-4-carboxamide,
  (d) 3-ethyl-5-(4-methyl-β-hydroxyphenethyl)-N-methylisoxazole-4-carboxamide,
  (e) 3-ethyl-5-(4-methoxy-β-hydroxyphenethyl)-N-methylisoxazole-4-carboxamide,
  (f) 3-ethyl-5-(3-fluoro-β-hydroxyphenethyl)-N-methylisoxazole-4-carboxamide,
  (g) 3-ethyl-5-(2-fluoro-β-hydroxyphenethyl)-N-methylisoxazole-4-carboxamide, or
  (h) 3-ethyl-5-(2-methyl-β-hydroxyphenethyl)-N-methylisoxazole-4-carboxamide, respectively.

EXAMPLE 2

3-Ethyl-N-methyl-5-phenacyl-4-isoxazole carboxamide.

A solution of 29.0 g. (0.105 mole) of 3-ethyl-5-(β-hydroxyphenethyl)-N-methyl-isoxazole-4-carboxamide and 500 ml. acetic acid at room temperature is treated dropwise rapidly with 12.5 g. (0.125 mole) of chromium trioxide in 125 ml. water. The resulting solution is stirred for 2 hours at room temperature and a portion of the acetic acid is removed in vacuo. The remainder is poured onto ice water and extracted with methylene chloride. The methylene chloride layer is washed with 2N sodium hydroxide, dried over anhydrous magnesium sulfate, filtered and evaporated in vacuo. The solid residue is triturated with ether and recrystallized from ethanol to give 3-ethyl-N-methyl-5-phenacyl-4-isoxazole carboxamide, m.p. 134° to 136° C.

Following the above procedure and using in place of 3-ethyl-5-(β-hydroxyphenethyl)-N-methyl-isoxazole-4-carboxamide, an equivalent amount of
  (a) 3-cyclohexyl-5-(β-hydroxyphenethyl)-N-methylisoxazole-4-carboxamide,
  (b) 3-ethyl-5-(4-chloro-β-hydroxyphenethyl)-N-methylisoxazole-4-carboxamide, (c) 3-ethyl-5-(4-fluoro-β-hydroxyphenethyl)-N-methylisoxazole-4-carboxamide,
  (d) 3-ethyl-5-(4-methyl-β-hydroxyphenethyl)-N-methyl-isoxazole-4-carboxamide,
  (e) 3-ethyl-5-(4-methoxy-β-hydroxyphenethyl)-N-methylisoxazole-4-carboxamide,
  (f) 3-ethyl-5-(3-fluoro-β-hydroxyphenethyl)-N-methylisoxazole-4-carboxamide,
  (g) 3-ethyl-5-(2-fluoro-β-hydroxyphenethyl)-N-methylisoxazole-4-carboxamide, or
  (h) 3-ethyl-5-(2-methyl-β-hydroxyphenethyl)-N-methylisoxazole-4-carboxamide,
there is obtained
  (a) 3-cyclohexyl-N-methyl-5-phenacyl-4-isoxazole carboxamide,
  (b) 3-ethyl-N-methyl-5-(4-chlorophenacyl)-4-isoxazole carboxamide,
  (c) 3-ethyl-N-methyl-5-(4-fluorophenacyl)-4-isoxazole carboxamide,
  (d) 3-ethyl-N-methyl-5-(4-methylphenacyl)-4-isoxazole carboxamide,
  (e) 3-ethyl-N-methyl-5-(4-methoxyphenacyl)-4-isoxazole carboxamide,
  (f) 3-ethyl-N-methyl-5-(3-fluorophenacyl)-4-isoxazole carboxamide,
  (g) 3-ethyl-N-methyl-5-(2-fluorophenacyl)-4-isoxazole carboxamide, or
  (h) 3-ethyl-N-methyl-5-(2-methylphenacyl)-4-isoxazole carboxamide, respectively.

EXAMPLE 3

3-Ethyl-5-methyl-6-phenyl-isoxazolo[4,5-c]pyridin-4(5H)-one.

A mixture of 11.0 g. (0.0405 mole) of 3-ethyl-N-methyl-5-phenacyl-4-isoxazole carboxamide and 120 ml. of 2M sulfuric acid is refluxed for 18 hours. The mixture is cooled and extracted with methylene chloride. The methylene chloride layer is washed with water and then brine, dried over anhydrous magnesium sulfate, filtered and evaporated in vacuo. The residue is triturated with ether and filtered to give 3-ethyl-5-methyl-6-phenyl-isoxazolo[4,5-c]pyridin4(5H)-one, m.p. 167° to 169° C.

Following the above procedure and using in place of 3-ethyl-N-methyl-5-phenacyl-4-isoxazole carboxamide, an equivalent amount of
(a) 3-cyclohexyl-N-methyl-5-phenacyl-4-isoxazole carboxamide,
(b) 3-ethyl-N-methyl-5-(4-chlorophenacyl)-4-isoxazole carboxamide,
(c) 3-ethyl-N-methyl-5-(4-fluorophenacyl)-4-isoxazole carboxamide,
(d) 3-ethyl-N-methyl-5-(4-methylphenacyl)-4-isoxazole carboxamide,
(e) 3-ethyl-N-methyl-5-(4-methoxyphenacyl)-4-isoxazole carboxamide,
(f) 3-ethyl-N-methyl-5-(3-fluorophenacyl)-4-isoxazole carboxamide,
(g) 3-ethyl-N-methyl-5-(2-fluorophenacyl)-4-isoxazole carboxamide,
or
(h) 3-ethyl-N-methyl-5-(2-methylphenacyl)-4-isoxazole carboxamide,
there is obtained
(a) 3-cyclohexyl-5-methyl-6-phenyl-isoxazolo[4,5-c]pyridin-4(5H)-one,
(b) 3-ethyl-5-methyl-6-(p-chlorophenyl)-isoxazolo[4,5-c]pyridin-4(5H)-one,
(c) 3-ethyl-5-methyl-6-(p-fluorophenyl)-isoxazolo[4,5-c]pyridin-4(5H)-one,
(d) 3-ethyl-5-methyl-6-(p-tolyl)-isoxazolo[4,5-c]pyridin-4(5H)-one,
(e) 3-ethyl-5-methyl-6-(p-anisyl)-isoxazolo[4,5-c]pyridin-4(5H)-one,
(f) 3-ethyl-5-methyl-6-(m-fluorophenyl)-isoxazolo[4,5-c]pyridin-4(5H)-one,
(g) 3-ethyl-5-methyl-6-(o-fluorophenyl)-isoxazolo[4,5-c]pyridin-4(5H)-one, or
(h) 3-ethyl-5-methyl-6-(o-tolyl)-isoxazolo[4,5-c]pyridin-4(5H)-one, respectively.

EXAMPLE 4

3-(1-iminopropyl)-4-hydroxy-6-phenyl-1-methyl-2(1H)-pyridone.

A mixture of 7.2 g. (0.0314 mole) of 3-ethyl-5-methyl-6-phenyl-isoxazolo[4,5-c]pyridin-4(5H)-one, 160 ml. ethanol and 0.800 g. 10% palladium on carbon is hydrogenated at 50 psi and room temperature. The hydrogenation is ceased after 1 equivalent of hydrogen is absorbed (ca 4 hours). The mixture is filtered to remove the catalyst and the solvent removed in vacuo. The residue is crystallized from ether to give 3-(1-iminopropyl)-4-hydroxy-6-phenyl-1-methyl-2(1H)-pyridone, m.p. 145° to 147° C.

Following the above procedure and using in place of 3-ethyl-5-methyl-6-phenyl-isoxazolo[4,5-c]pyridin-4(5H)-one, an equivalent amount of
(a) 3-cyclohexyl-5-methyl-6-phenyl-isoxazolo[4,5-c]pyridin-4(5H)-one,
(b) 3-ethyl-5-methyl-6-(p-chlorophenyl)-isoxazolo[4,5-c]pyridin-4(5H)-one,
(c) 3-ethyl-5-methyl-6-(p-fluorophenyl)-isoxazolo[4,5-c]pyridin-4(5H)-one,
(d) 3-ethyl-5-methyl-6-(p-tolyl)-isoxazolo[4,5-c]pyridin-4(5H)-one,
(e) 3-ethyl-5-methyl-6-(p-anisyl)-isoxazolo[4,5-c]pyridin-4(5H)-one,
(f) 3-ethyl-5-methyl-6-(m-fluorophenyl)-isoxazolo[4,5-c]pyridin-4(5H)-one,
(g) 3-ethyl-5-methyl-6-(o-fluorophenyl)-isoxazolo[4,5-c]pyridin-4(5H)-one, or
(h) 3-ethyl-5-methyl-6-(o-tolyl)-isoxazolo[4,5-c]pyridin-4(5H)-one,
there is obtained
(a) 3-(1-iminocyclohexylmethyl)-4-hydroxy-6-phenyl-1-methyl-2(1H)-pyridone,
(b) 3-(1-iminopropyl)-4-hydroxy-6-(p-chlorophenyl)-1-methyl-2(1H)-pyridone,
(c) 3-(1-iminopropyl)-4-hydroxy-6-(p-fluorophenyl)-1-methyl-2(1H)-pyridone,
(d) 3-(1-iminopropyl)-4-hydroxy-6-(p-tolyl)-1-methyl-2(1H)-pyridone,
(e) 3-(1-iminopropyl)-4-hydroxy-6-(p-anisyl)-1-methyl-2(1H)-pyridone,
(f) 3-(1-iminopropyl)-4-hydroxy-6-(m-fluorophenyl)-1-methyl-2(1H)-pyridone,
(g) 3-(1-iminopropyl)-4-hydroxy-6-(o-fluorophenyl)-1-methyl-2(1H)-pyridone, or
(h) 3-(1-iminopropyl)-4-hydroxy-6-(o-tolyl)-1-methyl-2(1H)-pyridone, respectively.

The 3-(1-iminopropyl)-4-hydroxy-6-phenyl-1-methyl-2(1H)-pyridone of this example is an effective minor tranquilizer and neuroleptic agent when orally administered to an animal in need of said treatment at a dosage of 100 mg. two to four times per day. The compound of this example is also effective as a sleep inducer when orally administered to an animal in need of said treatment at a dosage of 200 mg. just before bedtime.

What is claimed is:
1. A compound of the formula

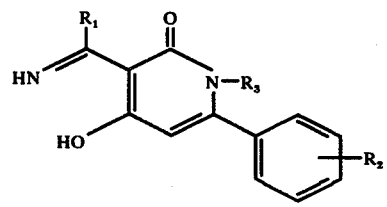

where
$R_1$ represents lower alkyl or cycloalkyl,
$R_2$ represents hydrogen, halo having an atomic weight of about 19 to 36, lower alkyl or alkoxy, and
$R_3$ represents straight chain lower alkyl,
or a pharmaceutically acceptable salt thereof.
2. A compound of the formula

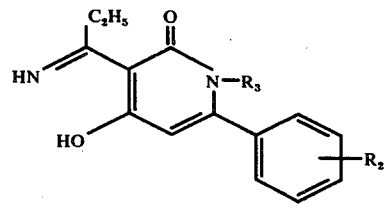

where $R_2$ and $R_3$ are as defined in claim 1, or a pharmaceutically acceptable salt thereof.
3. A compound of the formula

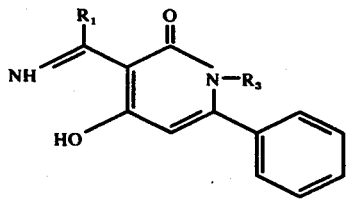

where $R_1$ and $R_3$ are as defined in claim 1, or a pharmaceutically acceptable salt thereof.

4. A compound of the formula

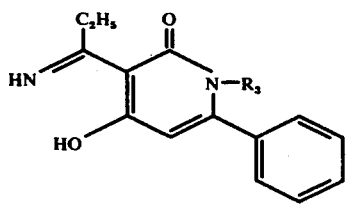

where $R_3$ is as defined in claim 1, or a pharmaceutically acceptable salt thereof.

5. The compound of claim 1 which is 3-(1-iminopropyl)-4-hydroxy-6-phenyl-1-methyl-2(1H)-pyridone.

6. The compound of claim 1 which is 3-(1-iminopropyl)-4-hydroxy-6-(p-fluorophenyl)-1-methyl-2(1H)-pyridone.

7. The compound of claim 1 which is 3-(1-iminopropyl)-4-hydroxy-6-(m-fluorophenyl)-1-methyl-2(1H)-pyridone.

8. The compound of claim 1 which is 3-(1-iminopropyl)-4-hydroxy-6-(o-fluorophenyl)-1-methyl-2(1H)-pyridone.

9. A pharmaceutical composition comprising an antipsychotic-effective amount of a compound of claim 1 and a pharmaceutically acceptable diluent or carrier therefor.

* * * * *